United States Patent
Ishii et al.

(10) Patent No.: US 8,278,476 B2
(45) Date of Patent: Oct. 2, 2012

(54) PROCESS FOR PRODUCING α-SUBSTITUTED ESTER

(75) Inventors: Akihiro Ishii, Kawagoe (JP); Manabu Yasumoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 12 days.

(21) Appl. No.: 13/127,955

(22) PCT Filed: Oct. 22, 2009

(86) PCT No.: PCT/JP2009/068161
§ 371 (c)(1),
(2), (4) Date: May 5, 2011

(87) PCT Pub. No.: WO2010/055755
PCT Pub. Date: May 20, 2010

(65) Prior Publication Data
US 2011/0213176 A1    Sep. 1, 2011

(30) Foreign Application Priority Data
Nov. 11, 2008    (JP) .................................. 2008-289205

(51) Int. Cl.
*C07C 69/612*    (2006.01)
(52) U.S. Cl. ...................................................... 560/105
(58) Field of Classification Search .................. None
See application file for complete search history.

(56) References Cited

U.S. PATENT DOCUMENTS
6,395,918 B1    5/2002    Loewenthal et al.

FOREIGN PATENT DOCUMENTS
ES    2 136 028 B1    11/1999
JP    2002-512999 A    5/2002
JP    2010-120919 A    6/2010

OTHER PUBLICATIONS

Green et al., "Protective Groups in Organic Synthesis", Third Edition, 1999, John Wiley & Sons, Inc. (twenty-six (26) pages).
Studte et al., "Zinc-Catalyzed Enantiospecfic sp3-sp3 Cross-Coupling of alpha-Hydroxy Ester Triflates with Grignard Reagent", Angewandte Chemie International Edition (Germany), 2008, vol. 47, pp. 5451-5455.
Kinkead et al., "Reactions of Polyfluoroalkyl Fluorosulfates with Nucleophiles: An Unusual Substitution at the Sulfur-Fluorine Base", Journal of the American Chemical Society (U.S), 1984. vol. 106, pp. 7496-7500.
Forms PCT/ISA/210 (five (5) pages) and PCT/ISA/237 (three (3) pages) dated Dec. 8, 2009.

*Primary Examiner* — Paul A Zucker
(74) *Attorney, Agent, or Firm* — Crowell & Moring LLP

(57) ABSTRACT

There is provided a process for producing an α-substituted ester by reaction of a fluorosulfuric acid ester of α-hydroxyester with a Grignard reagent in the presence of a zinc catalyst. It is newly found that the reaction for production of α-substituted esters, in which the raw reaction substrate is limited to expensive trifluoromethanesulfonic acid esters, can proceed favorably with the use of fluorosulfuric acid esters suitable for mass-production uses. By the use of the fluorosulfuric acid ester high in optical purity, it is possible to obtain the α-substituted ester with high optical purity upon inversion of the asymmetric carbon configuration. The process of the present invention can solve all of the prior art problems and can be applied for industrial uses.

6 Claims, No Drawings

PROCESS FOR PRODUCING α-SUBSTITUTED ESTER

TECHNICAL FIELD

The present invention relates to a process for producing α-substituted esters, which are important as intermediates for pharmaceutical and agricultural chemicals.

BACKGROUND ART

It is known that α-substituted esters are important as intermediates for pharmaceutical and agricultural chemicals. There have been reported, as conventional production techniques relevant to the present invention, a process of producing an optically active α-substituted ester by reaction of a trifluoromethanesulfonic acid ester of optically active α-hydroxyester with a Grignard reagent in the presence of a zinc catalyst (see Non-Patent Document 1). Various substitution reactions of fluorosulfuric acid esters of alcohols with nucleophilic reagents have also been reported (see Patent Document 1 and Non-Patent Document 2).

PRIOR ART DOCUMENTS

Patent Documents
    Patent Document 1: Spanish Patent No. 2136028

Non-Patent Documents
    Non-Patent Document 1: Angewandte Chemie International Edition (Germany), 2008, Vol. 47, P. 5451-5455
    Non-Patent Document 2: Journal of the American Chemical Society (U.S.), 1984, Vol. 106, P. 7496-7500

DISCLOSURE OF THE INVENTION

It is an object of the present invention to provide a practical production process of α-substituted esters. In order to achieve the object of the present invention, it is necessary to solve the following problems in the prior art techniques.

The process of Non-Patent Document 1 is considered as an easy and practical process for small-scale production use in view of the advantages that: cheap zinc chloride can be used as the catalyst; severe reaction conditions such as extreme low-temperature conditions are not required; and the target product can be obtained with high yield and high inversion rate. This production process is not however suitable for large-scale production use as it is necessary to use very expensive trifluoromethanesulfonic acid anhydride $[(CF_3SO_2)_2O]$ for the preparation of the trifluoromethanesulfonic acid ester as the raw material substrate. Further, trifluoromethanesulfonic acid $(CF_3SO_3H)$ and salt thereof are stoichiometrically generated as by-products during the raw material substrate preparation and substitution reaction and raise a problem of waste disposal due to their poor decomposition properties.

It is known in Patent Document 1 and Non-Patent Document 2 that different types of substitution reactions occur depending on the kinds and combinations of the fluorosulfuric acid esters and nucleophilic reagents used (see Scheme 1). However, almost no substitution reactions with carbon nucleophilic reagents are known. There has been no report made on the target reaction of the present invention, i.e., the substitution reaction of a fluorosulfuric acid ester of α-hydroxyester with a Grignard reagent in the presence of a zinc catalyst. It has been unknown whether the substitution reaction occurs favorably via a desired Type-A route for production of the target α-substituted ester of the present invention. It has also been unknown whether the target product can be obtained with high inversion rate from an optically active raw material substrate.

Scheme 1

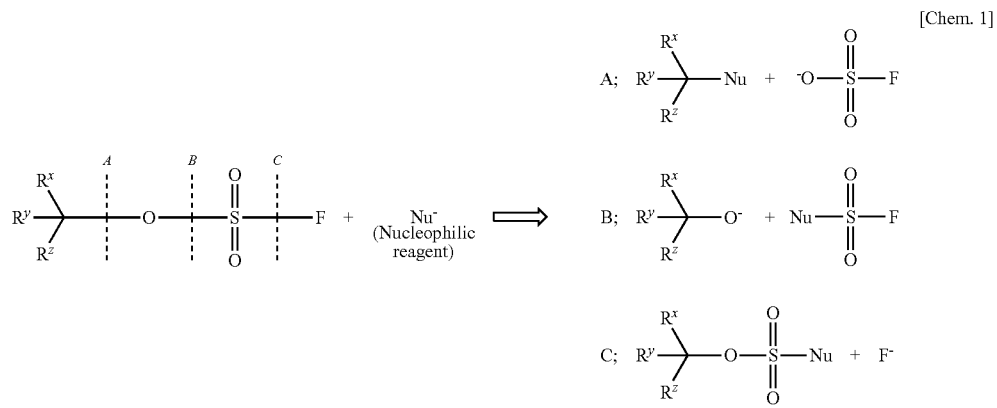

Type A: Formation of C — Nu bond upon cleavage of C — O bond
Type B: Formation of Nu — S bond upon cleavage of O — S bond
Type C: Formation of S — Nu bond upon cleavage of S — F bond As mentioned above, there has been a strong demand for a production process which is as practical as that of Non-Patent Document 1 and, at the same time, is suitably applicable for mass production of α-substituted esters (with the use of a raw material substrate that can be prepared at low cost and with no problem of waste disposal).

The present inventors have made extensive researches in view of the above problems and, as a result, have found that it is possible to produce an α-substituted ester by reaction of a fluorosulfuric acid ester of α-hydroxyester with a Grignard reagent in the presence of a zinc catalyst. It is preferable that the raw material substrate has an alkyl group or a substituted alkyl group, more preferably methyl group, as an α-position substituent group and contains an alkyl ester, more preferably $C_1$-$C_6$ lower alkyl ester, as an ester moiety. Further, the raw material substrate is preferably in the form of an optically active substance, more preferably any of those prepared from (S)-lactates; and the configuration of the asymmetric carbon of the raw material substrate is inverted in the reaction. It is preferable that the zinc catalyst has, as a ligand, a chlorine atom, an acetate group ($CH_3CO_2$) or a triflate group ($CF_3SO_3$). As the zinc catalyst, zinc chloride is particularly preferred. It is also preferable that the Grignard reagent has an alkyl group or a substituted alkyl group, more preferably alkyl group, as a nucleophilic moiety. Among others, a magnesium chloride reagent is particularly preferred as the Grignard reagent.

The present inventors have further found that it is possible that the fluorosulfuric acid ester, which is suitable for large-scale production use, can suitably be utilized as the raw material substrate in the substitution reaction of Non-Patent Document 1 in place of the trifluoromethanesulfonic acid ester.

In this way, the present inventors have found the particularly useful techniques for production of the α-substituted ester. The present invention is based on these findings.

Namely, the present invention provides a practical process for producing an α-substituted ester as set forth below in Inventive Aspects 1 to 4.

[Inventive Aspect 1]

A process for producing an α-substituted ester of the general formula [4], comprising: reacting a fluorosulfuric acid ester of α-hydroxyester of the general formula [1] with a Grignard reagent of the general formula [3] in the presence of a zinc catalyst of the general formula [2]

[Chem. 2]

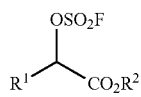
[1]

[Chem. 3]

[2]

[Chem. 4]

[3]

[Chem. 5]

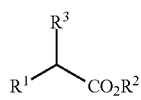
[4]

where $R^1$ represents a hydrogen atom, an alkyl group, a substituted alkyl group, an alkenyl group, a substituted alkenyl group, an alkynyl group, a substituted alkynyl group, an aromatic ring group, or a substituted aromatic ring group; $R^2$ represents an alkyl group or a substituted alkyl group; $R^3$ represents an alkyl group, a substituted alkyl group, an alkenyl group, a substituted alkenyl group, an alkynyl group, a substituted alkynyl group, an aromatic ring group, or a substituted aromatic ring group; when $R^1$ is any substituent group other than hydrogen atom, $R^1$ and $R^2$ may form a ring structure by a covalent bond between carbon atoms thereof through or without a heteroatom; $X^1$ represents a fluorine atom, a chlorine atom, a bromine atom, an iodine atom, an acetate group ($CH_3CO_2$), or a triflate group ($CF_3SO_3$); and $X^2$ represents a chlorine atom, a bromine atom or an iodine atom.

[Inventive Aspect 2]

A process for producing an optically active α-substituted ester of the general formula [8], comprising: reacting a fluorosulfuric acid ester of optically active α-hydroxyester of the general formula [5] with a Grignard reagent of the general formula [7] in the presence of a zinc catalyst of the general formula [6]

[Chem. 6]

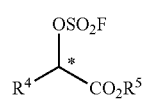
[5]

[Chem. 7]

[6]

[Chem. 8]

[7]

[Chem. 9]

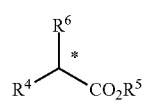
[8]

where $R^4$ represents an alkyl group or a substituted alkyl group; $R^5$ represents an alkyl group; $R^6$ represents an alkyl group or a substituted alkyl group; $R^4$ and $R^5$ may form a ring structure by a covalent bond between carbon atoms thereof through or without a heteroatom; $X^3$ represents a chlorine atom, an acetate group ($CH_3CO_2$) or a triflate group ($CF_3SO_3$); and * represents an asymmetric carbon atom whose configuration is inverted in the reaction.

[Inventive Aspect 3]

A process for producing an optically active α-substituted ester of the general formula [12], comprising: reacting a fluorosulfuric acid ester of optically active α-hydroxyester of the general formula [9] with a Grignard reagent of the general formula [11] in the presence of a zinc catalyst of the general formula [10]

[Chem. 10]

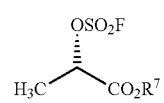
[9]

[Chem. 11]

[10]

[Chem. 12]

[11]

[Chem. 13]

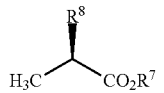
[12]

where $R^7$ represents a $C_1$-$C_6$ lower alkyl group; and $R^8$ represents an alkyl group.

[Inventive Aspect 4]

The process according to any one of Inventive Aspects 1 to 3, further comprising: forming the fluorosulfuric acid ester of α-hydroxyester by reaction of an alcohol of the formula [1a], [5a] or [9a] with sulfuryl fluoride ($SO_2F_2$) in the presence of a base and water

[Chem. 14]

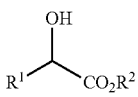

[1a]

[Chem. 15]

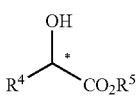

[5a]

[Chem. 16]

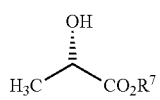

[9a]

wherein $R^1$, $R^2$, $R^4$, $R^5$, $R^7$ and * have the same definitions as in the formulas [1], [5] and [9].

DETAILED DESCRIPTION

The advantages of the present invention over the prior art techniques will be explained below.

The raw material substrate of the present invention, i.e., fluorosulfuric acid ester of α-hydroxyester may be prepared with the use of fluorosulfuric acid anhydride [$(FSO_2)_2O$] in a similar manner as described in Patent Document 1 etc. It is however preferable to prepare the fluorosulfuric acid ester of α-hydroxyester by a method described in "Process for Producing Fluorosulfuric Acid Ester" (Japanese Patent Application No. 2008-272020, hereinafter referred to as "prior application"), which has already been filed by the present applicant, in view of the low-cost preparation of the raw material substrate suitable for large-scale production use. The combination of the present invention with the prior application is particularly effective.

As the prior application has not yet been laid open at the time of filing of the present application, a brief explanation of the prior application will be given below. (The detail of the prior application will be explained later in "Best Mode for Carrying out the Invention" as well as Reference Example 1). The prior application provides a process for producing a fluorosulfuric acid ester by reaction of an alcohol with sulfuryl fluoride ($SO_2F_2$) in the presence of a base and water. The production process of the fluorosulfuric acid ester according to the prior application is characterized in that the reaction is preferably performed in a two-phase system with the use of a reaction solvent inmiscible with water. The reaction reagent of the prior application, sulfuryl fluoride, is widely used as a fumigant and available in a large quantity at low cost. The use of such a reagent enables low-cost preparation of the fluorosulfuric acid ester of α-hydroxyester as the raw material substrate of the present invention.

In the present invention, fluorosulfuric acid ($FSO_3H$) and salt thereof are stoichiometrically generated as by-products during the substitution reaction. These compounds can however be readily processed to sodium fluoride, potassium fluoride, calcium fluoride, sodium sulfate, potassium sulfate, calcium sulfate etc., which raise no problem of waste disposal, by reaction of an inorganic base (such as sodium hydroxide, potassium hydroxide or calcium hydroxide) or aqueous solution thereof. Also from this perspective, the process of the present invention is considered to be suitable for mass-production use. Further, the preparation of the raw material substrate according to the prior application is suitable in view of waste proposal. Although the fluorosulfuric acid anhydride has two fluorosulfonyl groups ($FSO_2$), only one of the fluorosulfonyl groups of the fluorosulfuric acid anhydride is introduced into the raw material substrate i.e. fluorosulfuric acid ester of α-hydroxyester; and the other fluorosulfonyl group functions as a leaving group during the introduction of the one fluorosulfonyl group into the fluorosulfuric acid ester of α-hydroxyester. The sulfuryl fluoride has high atom economy as an agent for introduction of the fluorosulfonyl group and allows a significant reduction in waste throughout the production process including the preparation of the raw material substrate.

Furthermore, it has been newly found that, in the present invention, the substitution reaction of the raw material substrate i.e. fluorosulfuric acid ester of α-hydroxyester with the hard Grignard reagent in the presence of the zinc catalyst occurs selectively via a desired Type-A route in preference to Type-B and Type-C routes of Scheme 1. It has also been found that the reaction of the fluorosulfuric acid ester of optically active α-hydroxyester proceeds with high inversion rate so that the optically active α-substituted ester, which is very important as the intermediates for pharmaceutical and agricultural chemicals, can be obtained with high yield.

In the present invention, the target product can be obtained with high chemical purity as almost no difficult-to-separate impurities occur as by-products. The α-substituted ester can be obtained with high optical purity by the use of the fluorosulfuric acid ester of optically active α-hydroxyester high in optical purity.

As mentioned above, the production process of the present invention solves all of the prior art problems and can be applied for industrial uses.

The production process of the α-substituted ester according to the present invention will be described in detail below.

In the present invention, an α-substituted ester of the general formula [4] is produced by reaction of a fluorosulfuric acid ester of α-hydroxyester of the general formula [1] with a Grignard reagent of the general formula [3] in the presence of a zinc catalyst of the general formula [2].

In the fluorosulfuric acid ester of α-hydroxyester of the general formula [1], $R^1$ represents a hydrogen atom, an alkyl group, a substituted alkyl group, an alkenyl group, a substituted alkenyl group, an alkynyl group, a substituted alkynyl group, an aromatic ring group, or a substituted aromatic ring group. Among others, $R^1$ is preferably an alkyl group or a substituted alkyl group, more preferably methyl group.

The alkyl group can have 1 to 18 carbon atoms and can be in the form of a linear or branched structure, or a cyclic structure (in the case of 3 or more carbon atoms). The alkenyl group refers to a group in which any number of single bonds between any two adjacent carbon atoms of the above alkyl group has been replaced with a double bond. In this case, the double bond can be in an E-isomer configuration, a Z-isomer configuration or a mixture thereof (the alkenyl carbon ($SP^2$ carbon) may not be linked directly to the carbon to which the fluorosulfonyloxy group ($FSO_2O$) is bonded). The alkynyl group refers to a group in which any number of single bonds between any two adjacent carbon atoms of the above alkyl group has been replaced with a triple bond (the alkynyl carbon (SP carbon) may not be linked directly to the carbon to which the fluorosulfonyloxy group is bonded). The aromatic ring group can have 1 to 18 carbon atoms and can be an aromatic hydrocarbon group, such as phenyl, naphthyl or anthryl, or an aromatic heterocyclic group containing a heteroatom e.g. nitrogen, oxygen or sulfur, such as pyrrolyl, furyl, thienyl, indolyl, benzofuryl or benzothienyl.

Any of the carbon atoms of the alkyl group, the alkenyl group, the alkynyl group and the aromatic ring group may be replaced with any number of and any combination of substituents (which correspond to the substituted alkyl group, the substituted alkenyl group, the substituted alkynyl group and the substituted aromatic ring group, respectively). Examples of such substituents are: halogen atoms such as fluorine, chlorine, bromine and iodine; azide group; nitro group; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; lower alkylamino groups such as dimethylamino, diethylamino and dipropylamino; lower alkylthio groups such as methylthio, ethylthio and propylthio; cyano group; lower alkoxycarbonyl groups such as methoxycarbonyl, ethoxycarbonyl and propoxycarbonyl; aminocarbonyl group ($CONH_2$); lower alkylaminocarbonyl groups such as dimethylaminocarbonyl, diethylaminocarbonyl and dipropylaminocarbonyl; unsaturated groups such as lower alkenyl groups and lower alkynyl groups; aromatic ring groups such as phenyl, naphthyl, pyrrolyl, furyl and thienyl; aromatic ring oxy groups such as phenoxy, naphthoxy, pyrrolyloxy, furyloxy and thienyloxy; aliphatic heterocyclic groups such as piperidyl, piperidino and morpholinyl; hydroxyl group; protected hydroxyl groups; amino group; protected amino groups (including amino acids and peptide residues); thiol group; protected thiol groups; aldehyde group; protected aldehyde groups; carboxyl group; and protected carboxyl groups.

The following terms are herein defined by the following meanings in the present specification. The term "lower" means that the group to which the term is attached has 1 to 6 carbon atoms in the form of a linear structure, a branched structure or a cyclic structure (in the case of 3 carbons or more). It means that, when the "unsaturated group" is a double bond (alkenyl group), the double bond can be in an E-isomer configuration, a Z-isomer configuration or a mixture thereof. It means that the "protected hydroxyl, amino, thiol, aldehyde and carboxyl groups" may be those having protecting groups as described in "Protective Groups in Organic Synthesis", Third Edition, 1999, John Wiley & Sons, Inc. (In this case, two or more functional groups may be protected with one protecting group.) Further, the "unsaturated group", "aromatic ring group", "aromatic ring oxy group" and "aliphatic heterocyclic group" may be substituted with halogen atoms, azide group, nitro group, lower alkyl groups, lower haloalkyl groups, lower alkoxy groups, lower haloalkoxy groups, lower alkylamino groups, lower alkylthio groups, cyano group, lower alkoxycarbonyl groups, aminocarbonyl group, lower aminocarbonyl groups, hydroxyl group, protected hydroxyl groups, amino group, protected amino groups, thiol group, protected thiol groups, aldehyde group, protected aldehyde groups, carboxyl group or protected carboxyl groups. Although some of these substituent groups may react with the Grignard reagent in the presence of the zinc, the desired reaction can be promoted favorably by adoption of the suitable reaction conditions.

In the fluorosulfuric acid ester of α-hydroxyester of the general formula [1], $R^2$ represents an alkyl group or a substituted alkyl group. Examples of the alkyl group and substituted alkyl group usable as $R^2$ are the same as those of $R^1$ in the fluorosulfuric acid ester of α-hydroxyester of the general formula [1]. Among others, $R^2$ is preferably an alkyl group, more preferably a $C_1$-$C_6$ lower alkyl group.

When $R^1$ is any substituent group other than hydrogen atom in the fluorosulfuric acid ester of α-hydroxyester of the general formula [1], two substituent groups $R^1$ and $R^2$ may form a ring structure by a covalent bond between carbon atoms thereof through or without a heteroatom (such as nitrogen, oxygen, sulfur etc.) (that is, the fluorosulfuric acid ester may be, for example, an fluorosulfuric acid ester of α-hydroxylactone).

The carbon atom to which the fluorosulfonyloxy group is bonded is an asymmetric carbon atom when $R^1$ is any substituent group other than hydrogen in the fluorosulfuric acid ester of α-hydroxyester of the general formula [1]. The configuration of this asymmetric carbon atom is inverted in the reaction. In the case of an optically active substance being desired as the target product, a fluorosulfuric acid ester of optically active α-hydroxyester is used as the raw material substrate. (It is needless to say that the raw material substrate can be a racemic mixture depending on the target product.)

In the zinc catalyst of the general formula [2], $X^1$ represents a fluorine atom, a chlorine atom, a bromine atom, an iodine atom, an acetate group or a triflate group. Among others, $X^1$ is preferably a chlorine atom, an acetate group or a triflate group, more preferably a chlorine atom.

In the Grignard reagent of the general formula [3], $R^3$ represents an alkyl group, a substituted alkyl group, an alkenyl group, a substituted alkenyl group, an alkynyl group, a substituted alkynyl group, an aromatic ring group or a substituted aromatic ring group. Examples of the alkyl group, substituted alkyl group, alkenyl group, substituted alkenyl group, alkynyl group, substituted alkynyl group, aromatic ring group and substituted aromatic ring group usable as $R^3$ are the same as those of $R^1$ in the fluorosulfuric acid ester of α-hydroxyester of the general formula [1]. Among others, an alkyl group and a substituted alkyl group are preferred. Particularly preferred is an alkyl group.

In the Grignard reagent of the general formula [3], $X^2$ represents a chlorine atom, a bromine atom or an iodine atom. Among others, $X^2$ is preferably a chlorine atom.

In the fluorosulfuric acid ester of optically active α-hydroxyester of the general formula [5], $R^4$ and $R^5$ may form a ring structure by a covalent bond between carbon atoms thereof through or without a heteroatom (such as nitrogen, oxygen, sulfur etc.) (that is, the fluorosulfuric acid ester may be, for example, an fluorosulfuric acid ester of optically active α-hydroxylactone).

Further, * represents an asymmetric carbon atom in the fluorosulfuric acid ester of optically active α-hydroxyester of the general formula [5]. The configuration of this asymmetric carbon atom is inverted in the reaction. The fluorosulfuric acid ester of optically active α-hydroxyester of the general formula [5] can be in R-configuration and/or S-configuration. The configuration of the fluorosulfuric acid ester of optically active α-hydroxyester of the general formula [5] can be selected as appropriate depending on the configuration of the target product. It suffices that the optical purity of the fluorosulfuric acid ester of optically active α-hydroxyester of the general formula [5] is 75% ee or higher. The optical purity of the fluorosulfuric acid ester of optically active α-hydroxyester of the general formula [5] is generally preferably 80% ee or higher, more preferably 85% ee or higher.

Herein, the indication of the bond between the fluorosulfonyloxy group and the asymmetric carbon atom in the fluorosulfuric acid ester of optically active α-hydroxyester of the general formula [9] means that fluorosulfonyloxy group is directed to the bottom side of the paper.

It suffices that the optical purity of the fluorosulfuric acid ester of optically active α-hydroxyester of the general formula [9] is 80% ee or higher. The optical purity of the fluorosulfuric acid ester of optically active α-hydroxyester of the general formula [9] is generally preferably 85% ee or higher, more preferably 90% ee or higher.

The indication of the bond between $R^8$ and the asymmetric carbon atom in the optically active α-substituted ester of the general formula [12] means that $R^8$ is directed to the top side of the paper.

The fluorosulfuric acid ester of α-hydroxyester of the general formula [1] can be prepared from a known or commercially available α-hydroxyester, or an optically active substance thereof as required, by a similar method to those of Patent Document 1, Japanese Patent Application No. 2008-272020 and the like. For example, fluorosulfuric acid ester of (S)-ethyl lactate used in Example 1 was prepared in the same manner as in Reference Example 1.

It suffices to use the zinc catalyst of the general formula [2] in an amount of 0.7 mol or less, per 1 mol of the fluorosulfuric acid ester of α-hydroxyester of the general formula [1]. The amount of the zinc catalyst of the general formula [2] is preferably 0.0001 to 0.5 mol, more preferably 0.001 to 0.3 mol, per 1 mol of the fluorosulfuric acid ester of α-hydroxyester of the general formula [1].

Further, it suffices to use the Grignard reagent of the general formula [3] in an amount of 0.7 mol or more, per 1 mol of the fluorosulfuric acid ester of α-hydroxyester of the general formula [1]. The amount of the Grignard reagent of the general formula [3] is preferably 0.8 to 10 mol, more preferably 0.9 to 5 mol, per 1 mol of the fluorosulfuric acid ester of α-hydroxyester of the general formula [1].

Examples of the reaction solvent are: aliphatic hydrocarbon solvents such as n-hexane, cyclohexane and n-heptane; aromatic hydrocarbon solvents such as benzene, toluene and xylene; and ether solvents such as diethyl ether, tetrahydrofuran, diisopropyl ether, tert-butyl methyl ether, di-n-butyl ether, diethoxymethane and 1,2-dimethoxyethane. Among others, n-hexane, n-heptane, toluene, xylene, diethyl ether, tetrahydrofuran, tert-butyl methyl ether, di-n-butyl ether and 1,2-dimethoxyethane are preferred. Particularly preferred are n-heptane, toluene, xylene, diethyl ether, tetrahydrofurane and tert-butyl methyl ether. These reaction solvents can be used solely or in combination thereof.

It suffices to use the reaction solvent in an amount of 0.01 L (liter) or more per 1 mol of the fluorosulfuric acid ester of α-hydroxyester of the general formula [1]. The amount of the reaction solvent used is generally preferably 0.03 to 30 L, more preferably 0.05 to 20 L, per 1 mol of the fluorosulfuric acid ester of α-hydroxyester of the general formula [1].

It suffices that the reaction temperature is in the range of −80 to +80° C. The reaction temperature is preferably −40 to +40° C., more preferably −20 to +20° C.

Further, it suffices that the reaction time is 48 hours or less. As the reaction time depends on the raw substrate and the reaction conditions, it is preferable to determine the time at which the raw substrate has almost disappeared as the end of the reaction while monitoring the progress of the reaction by any analytical means such as gas chromatography, liquid chromatography or nuclear magnetic resonance.

The α-substituted ester of the general formula [4] can be obtained as a crude produce by post treatment of the reaction terminated liquid. As one example of post treatment operation, it is feasible to add water, an aqueous solution of inorganic acid (such as ammonium chloride, hydrochloric acid, hydrobromic acid, hydroiodic acid, nitric acid or sulfuric acid) or an aqueous solution of inorganic base (such as sodium hydrogencarbonate, potassium hydrogencarbonate, sodium carbonate, potassium carbonate, sodium hydroxide or potassium hydroxide) to the reaction terminated liquid, extract the resulting liquid with an organic solvent (such as n-hexane, n-heptane, toluene, xylene, methylene chloride, diisopropyl ether, tert-butyl methyl ether or ethyl acetate), wash the recovered organic layer with water, an aqueous inorganic acid solution or an aqueous inorganic base solution as required, dry the organic layer with a drying agent (such as anhydrous sodium sulfate or anhydrous magnesium sulfate), and then, concentrate the organic layer. Further, the crude product can be purified to a high chemical purity, as required, by purification operation such as activated carbon treatment, distillation, recrystallization or column chromatography.

As described above, the α-substituted ester is produced by reaction of the fluorosulfuric acid ester of α-hydroxyester with the Grignard reagent in the presence of the zinc catalyst (Inventive Aspect 1).

Among Inventive Aspect 1, the following material combination is preferred (Inventive Aspect 2): the raw substrate is in the form of an optically active substance having an alkyl group or a substituted alkyl group as an α-position substituent group and containing an alkyl ester moiety; the zinc catalyst is in the form of a compound having a chlorine atom, an acetate group or a triflate group as a ligand; and the Grignard reagent is a magnesium chloride reagent having a nucleophilic moiety with an alkyl group or a substituted alkyl group. It is advantageous in this aspect in that: the raw material substrate, zinc catalyst and Grignard reagent are relatively readily available; and the obtained optically active α-substituted ester is particularly important as an intermediate for pharmaceutical and agricultural chemicals.

Among Inventive Aspect 2, the following material combination is particularly preferred (Inventive Aspect 3): the raw material is in the form of an optically active substance of S-configuration having a methyl group as an α-position substituent group and containing a $C_1$-$C_6$ lower alkyl ester as an ester moiety; the zinc catalyst is zinc chloride; and the Grignard reagent is an alkyl magnesium chloride reagent. It is advantageous in this aspect in that: the raw material substrate, zinc catalyst and Grignard reagent are readily available; and the obtained optically active α-substituted ester is extremely important as an intermediate for pharmaceutical and agricultural chemicals.

Next, the process for preparation of the fluorosulfuric acid ester of (optically active) α-hydroxyester of the general formula [1], [5], [9] as the raw material of the present invention will be explained below. In the present invention, the fluorosulfuric acid ester of α-hydroxyester can be prepared by any process. It is however particularly desirable to prepare the fluorosulfuric acid ester of α-hydroxyester by the process of the prior application (Japanese Patent Application No. 2008-272020), as mentioned above, for preparation of the raw material at low cost and on a large scale. More specifically, the fluorosulfuric acid ester of α-hydroxyester can be prepared efficiently by reaction of an alcohol of the formula [1a], [5a]

or [9a] with sulfuryl fluoride ($SO_2F_2$) in the presence of a base and water (Inventive Aspect A).

[Chem. 17]

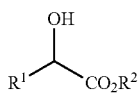

[1a]

[Chem. 18]

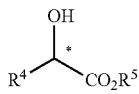

[5a]

[Chem. 19]

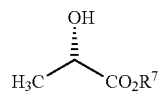

[9a]

In the above formulas, $R^1$, $R^2$, $R^4$, $R^5$, $R^7$ and * have the same definitions as in the formulas [1], [5] and [9].

The reaction is preferably preformed in a two-phase system with the use of a reaction solvent inmiscible with water (Inventive Aspect B).

Both of Inventive Aspects A and B are characterized in that the reaction of the alcohol and sulfuryl fluoride is performed in the presence of the base and water. It is possible by these characteristic features to effectively prevent the generation of "a fluorinated compound" by substitution of "—F" for "—$OSO_2F$" of the fluorosulfuric acid ester so that the fluorosulfuric acid ester can be obtained with high yield.

As the above-mentioned Japanese Patent Application No. 2008-272020 (prior application) has not yet laid open at the time of filing the present application, a detailed explanation of the aspects of the prior application will be given below.

[Inventive Aspect A]

A process for producing a fluorosulfuric acid ester of the general formula [2], comprising: reacting an alcohol of the general formula [1] with sulfuryl fluoride ($SO_2F_2$) in the presence of a base and water.

[Chem. 20]

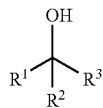

[1]

[Chem. 21]

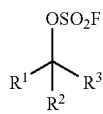

[2]

In the above formulas, $R^1$, $R^2$ and $R^3$ each independently represent a hydrogen atom, an alkyl group, a substituted alkyl group, an alkenyl group, a substituted alkenyl group, an alkynyl group, a substituted alkynyl group, an aromatic ring group, a substituted aromatic ring group, an alkylcarbonyl group, a substituted alkylcarbonyl group, an arylcarbonyl group, a substituted arylcarbonyl group, an alkoxycarbonyl group, a substituted alkoxycarbonyl group, an aminocarbonyl group, an alkylaminocarbonyl group, a substituted alkylaminocarbonyl group, an arylaminocarbonyl group, a substituted arylaminocarbonyl group or a cyano group. When none or one of the substituent groups $R^1$, $R^2$ and $R^3$ is hydrogen atom or cyano group, two of the substituent groups $R^1$, $R^2$ and $R^3$ may form a ring structure by a covalent bond between carbon atoms thereof through or without a heteroatom.

[Inventive Aspect B]

The process for producing the fluorosulfuric acid ester according to Inventive Aspect A, wherein the reaction is performed in a two-phase system with the use of a reaction solvent inmiscible with water. (In this prior application, the term "two-phase system" means that the reaction system has two liquid phases. In the strict sense, the reaction system has three phases in total including a gas phase in which sulfuryl fluoride exists.)

Examples of the alkyl group, alkenyl group, alkynyl group and aromatic ring group usable as $R^1$, $R^2$ and $R^3$ in the alcohol of the general formula [1] are the same as those of $R^1$ in the fluorosulfuric acid ester of α-hydroxyester of the general formula [1]. The alkyl moiety (R) of the alkylcarbonyl group (COR) has the same definition as that of the alkyl group of the present invention. The aryl moiety (Ar) of the arylcarbonyl group (COAr) has the same definition as that of the aromatic ring group of the present invention. The alkyl moiety (R) of the alkoxycarbonyl group ($CO_2R$) has the same definition as that the alkyl group of the present invention. The aminocarbonyl group refers to $CONH_2$. The alkyl moiety (R) of the alkylaminocarbonyl group (CONHR or $CONR_2$) has the same definition as that of the alkyl group of the present invention. The aryl moiety (Ar) of the arylaminocarbonyl group (CONHAr or $CONAr_2$) has the same definition as that of the aromatic ring group of present invention. The substituted alkyl group, the substituted alkenyl group, the substituted alkynyl group, the substituted aromatic ring group, the substituted alkylcarbonyl group, the substituted arylcarbonyl group, the substituted alkoxycarbonyl group, the substituted alkylaminocarbonyl group and the substituted arylaminocarbonyl group refers to those obtained by replacement of any of the carbon atoms of the alkyl group, the alkenyl group, the alkynyl group, the aromatic ring group, the alkylcarbonyl group, the arylcarbonyl group, the alkoxycarbonyl group, the alkylaminocarbonyl group and the arylaminocarbonyl group with any number of and any combination of substituents, such as halogen atoms, azide group, nitro group, lower alkyl groups, lower haloalkyl groups, lower alkoxy groups, lower haloalkoxy groups, lower alkylamino groups, lower alkylthio, cyano group, lower alkoxycarbonyl groups, aminocarbonyl group, lower alkylaminocarbonyl groups, unsaturated groups, aromatic ring groups, aromatic ring oxy groups, aliphatic heterocyclic groups, hydroxyl group, protected hydroxyl groups, amino group, protected amino groups, thiol group, protected thiol groups, aldehyde group, protected aldehyde groups, carboxyl group and protected carboxyl groups, as mentioned above for $R^1$ in the fluorosulfuric acid ester of α-hydroxyester of the general formula [1] of the present invention.

When all of the subsistent groups $R^1$, $R^2$ and $R^3$ are different in kind in the alcohol of the general formula [1], the carbon atom to which the hydroxyl group is bonded is an asymmetric carbon atom. The configuration of this asymmetric carbon atom is maintained throughout the reaction. The fluorosulfuric acid ester can be obtained with high optical purity by the use of the alcohol high in optical purity as the raw material substrate. The asymmetric carbon can be in R-configuration and/or S configuration. The configuration of the asymmetric carbon can be selected as appropriate depending on the configuration of the target product. It suffices that the optical purity is 70% ee or higher. The optical purity is generally preferably 80% ee or higher, more preferably 90% ee or higher.

It suffices to use the sulfuryl fluoride in an amount of 0.7 mol or more per 1 mol of the alcohol of the general formula [1]. The amount of the sulfuryl fluoride used is generally preferably 0.8 to 10 mol, more preferably 0.9 to 5 mol, per 1 mol of the alcohol of the general formula [1].

Examples of the base are: organic bases such as triethylamine, diisopropylethylamine, tri-n-propylamine, tri-n-butylamine, tri-n-pentylamine, pyridine, 2,3-lutidine, 2,4-lutidine, 2,6-lutidine, 3,4-lutidine, 3,5-lutidine, 2,4,6-collidine, 3,5,6-collidine, 4-dimethylaminopyridine, 1,5-diazabicyclo[4.3.0]non-5-ene (DBN), 1,8-diazabicyclo[5.4.0]undec-7-ene (DBU), N,N,N',N',N"-pentamethylguanidine, 1,5,7-triazabicyclo[4.4.0]dec-5-ene (TBD) and phosphazene bases e.g. BEMP and t-Bu-P4; and inorganic bases such as lithium hydrogencarbonate, sodium hydrogencarbonate, potassium hydrogencarbonate, lithium carbonate, sodium carbonate, potassium carbonate, lithium hydroxide, sodium hydroxide, potassium hydroxide and calcium hydroxide. The above bases can be used solely or in combination thereof.

It suffices to use the base in an amount of 0.7 mol or more per 1 mol of the alcohol of the general formula [1]. The amount of the base used is preferably 0.8 to 10 mol, more preferably 0.9 to 5 mol, per 1 mol of the alcohol of the general formula [1]. In the case of using two or more kinds of base materials in combination as the base, the amount of the base used refers to the total amount of these base materials.

It suffices to use the water in an amount of 0.05 L or more per 1 mol of the alcohol of the general formula [1]. The amount of the water used is preferably 0.1 to 30 L, more preferably 0.2 to 20 L, per 1 mol of the alcohol of the general formula [1].

Examples of the water-inmiscible reaction solvent are: aliphatic hydrocarbon solvents such as n-hexane, cyclohexane and n-heptane; aromatic hydrocarbon solvents such as benzene, toluene and xylene; halogenated hydrocarbon solvents such as methylene chloride, chloroform and 1,2-dichloroethane; ether solvents such as diethyl ether, diisopropyl ether and tert-butyl methyl ether; and ester solvents such as ethyl acetate and n-butyl acetate. The above reaction solvents can be used solely or in combination thereof.

It suffices to use the water-inmiscible reaction solvent in an amount of 0.01 L or more per 1 mol of the alcohol of the general formula [1]. The amount of the water-inmiscible reaction solvent used is preferably 0.03 to 30 L, more preferably 0.05 to 20 L, per 1 mol of the alcohol of the general formula [1].

It suffices that the reaction temperature is in the range of −10 to +150° C. The reaction temperature is preferably −5 to +125° C., more preferably 0 to +100° C.

Further, it suffices that the reaction time is 48 hours or less.

The target product can be obtained by ordinary post treatment operation of the reaction terminated liquid.

The prior application will be described in more detail below by way of the following reference example. It should be noted that the following reference example is not intended to limit the prior application thereto.

EXAMPLES

The present invention will be described in more detail below by way of the following examples. It should be noted that these examples are illustrative and are not intended to limit the present invention thereto.

Example 1

To 7.5 mL (0.33M) of tetrahydrofuran, 500 mg (2.50 mmol, 1.00 eq) of fluorosulfuric acid ester of optically active α-hydroxyester of the following formula (S-configuration, optical purity: 91.5% ee):

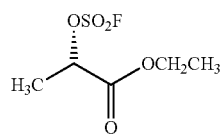

[Chem. 22]

and 0.12 mL (0.12 mmol, 0.05 eq) of 1.00M diethyl ether solution of zinc chloride (ZnCl$_2$) were added. The resulting solution was cooled to 0° C., followed by dropping 3.50 mL (3.47 mmol, 1.39 eq) of 0.99M tetrahydrofuran solution of benzyl magnesium chloride (C$_6$H$_5$CH$_2$MgCl) over 10 minutes into the solution. This reaction solution was stirred for 2 hours at 0° C. To the thus-obtained reaction terminated liquid, 20 mL of saturated aqueous ammonium chloride solution was added. The reaction terminated liquid was then extracted twice with 20 mL of n-hexane. The extracted organic layer was concentrated under a reduced pressure and subjected to vacuum drying. With this, 475 mg of a crude product of optically active α-substituted ester of the following formula (S-configuration):

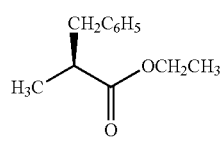

[Chem. 23]

was obtained. The yield of the crude product was 99%. It was confirmed by $^1$H-NMR analysis of the crude product that the conversion rate was 95% or higher (determined from the remaining amount of the raw material substrate).

The crude product was subjected to distillation under a reduced pressure (boiling point: ~100° C., vacuum degree: 0.4 kPa), thereby obtaining the optically active α-substituted ester as a purified product. The gas chromatographic purity of the purified product was 81.9%; and the optical purity of the purified product was determined by chiral gas chromatography to be 93.3% ee (S-configuration).

The $^1$H-NMR data of the optically active α-substituted ester are indicated below.

$^1$H-NMR [reference material: (CH$_3$)$_4$Si, deuterium solvent: CDCl$_3$] δ ppm; 1.15 (d, 6.8 Hz, 3H), 1.19 (t, 7.2 Hz, 3H), 2.70 (m, 2H), 3.02 (m, 1H), 4.09 (q, 7.2 Hz, 2H), 7.14-7.32 (Ar—H, 5H).

Reference Example 1

Into a pressure-proof reaction vessel of stainless steel (SUS) were placed 20.00 g (169.3 mmol, 1.00 eq) of optically active alcohol of the following formula (S-configuration):

[Chem. 24]

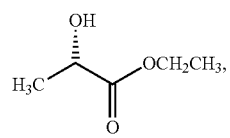

141 mL (1.20M) of toluene, 20.56 g (203.2 mmol, 1.20 eq) of triethylamine and 176.10 g of aqueous potassium carbonate solution (prepared from 35.10 g (254.0 mmol, 1.50 eq) of potassium carbonate and 141 mL (1.20M) of water). The reaction vessel was immersed in an ice cooling bath, followed by blowing 34.56 g (338.6 mmol, 2.00 eq) of sulfuryl fluoride from a cylinder into the reaction vessel. This reaction solution was stirred for 3 hours and 30 minutes under ice cooling conditions. It was confirmed by gas chromatography of the thus-obtained reaction terminated liquid (organic layer) that the conversion rate was 96%. At the time of measurement of the conversion rate, the gas chromatographic purity of optically active fluorosulfuric acid ester of the following formula (S-configuration):

[Chem. 25]

was 82.9%; and the gas chromatographic purity of optically active fluorinated compound of the following formula (R-configuration):

[Chem. 26]

was 4.4%. The generation ratio of the optically active fluorosulfuric acid ester and the optically active fluorinated compound was 95:5. It was further confirmed by chiral gas chromatography of the reaction terminated liquid (organic layer) that the optical purity of the optically active fluorosulfuric acid ester was 97.6% ee (S-configuration).

The reaction terminated liquid was separated into two layers. The recovered organic layer was subjected to distillation under a reduced pressure (boiling point: 89° C., vacuum degree: 3.6 kPa), thereby obtaining 21.13 g of the optically active fluorosulfuric acid ester as a purified product. The yield of the purified product was 62%. Further, the gas chromatographic purity of the purified product was 92.5%; and the optical purity of the purified product was 96.9% ee (S-configuration).

The $^1$H-NMR and $^{19}$F-NMR data of the optically active fluorosulfuric acid ester are indicated below.

$^1$H-NMR [reference material: $(CH_3)_4Si$, deuterium solvent: $CDCl_3$] δ ppm; 1.33 (t, 7.2 Hz, 3H), 1.72 (d, 6.9 Hz, 3H), 4.31 (q, 7.2 Hz, 2H), 5.22 (q, 6.9 Hz, 1H).

$^{19}$F-NMR [reference material: $C_6F_6$, deuterium solvent: $CDCl_3$] δ ppm; −63.40 (s, 1F).

The $^1$H-NMR and $^{19}$F-NMR data of the optically active fluorinated compound are indicated below.

$^1$H-NMR [reference material: $(CH_3)_4Si$, deuterium solvent: $CDCl_3$] δ ppm; 1.32 (t, 7.2 Hz, 3H), 1.58 (dd, 23.6 Hz, 6.9 Hz, 3H), 4.26 (q, 7.2 Hz, 2H), 5.00 (dq, 49.0 Hz, 6.9 Hz, 1H).

$^{19}$F-NMR [reference material: $C_6F_6$, deuterium solvent: $CDCl_3$] δ ppm; −21.88 (dq, 48.9 Hz, 24.4 Hz, 1F).

The invention claimed is:

1. A process for producing an α-substituted ester of the general formula [4], comprising: reacting a fluorosulfuric acid ester of α-hydroxyester of the general formula [1] with a Grignard reagent of the general formula [3] in the presence of a zinc catalyst of the general formula [2]

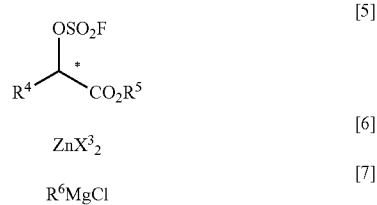

where $R^1$ represents a hydrogen atom, an alkyl group, a substituted alkyl group, an alkenyl group, a substituted alkenyl group, an alkynyl group, a substituted alkynyl group, an aromatic ring group, or a substituted aromatic ring group; $R^2$ represents an alkyl group or a substituted alkyl group; $R^3$ represents an alkyl group, a substituted alkyl group, an alkenyl group, a substituted alkenyl group, an alkynyl group, a substituted alkynyl group, an aromatic ring group, or a substituted aromatic ring group; when $R^1$ is any substituent group other than hydrogen atom, $R^1$ and $R^2$ may form a ring structure by a covalent bond between carbon atoms thereof through or without a heteroatom; $X^1$ represents a fluorine atom, a chlorine atom, a bromine atom, an iodine atom, an acetate group ($CH_3CO_2$), or a triflate group ($CF_3SO_3$); and $X^2$ represents a chlorine atom, a bromine atom or an iodine atom.

2. The process according to claim 1, wherein a fluorosulfuric acid ester of optically active α-hydroxyester of the general formula [5], a Grignard reagent of the general formula [7] and a zinc catalyst of the general formula [6] are used as the fluorosulfuric acid ester, the Grignard reagent and the zinc catalyst, respectively; and wherein an optically active α-substituted ester of the general formula [8] is produced as the α-substituted ester

[5]

[6]

[7]

-continued

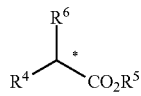
[8]

where $R^4$ represents an alkyl group or a substituted alkyl group; $R^5$ represents an alkyl group; $R^6$ represents an alkyl group or a substituted alkyl group; $R^4$ and $R^5$ may form a ring structure by a covalent bond between carbon atoms thereof through or without a heteroatom; $X^3$ represents a chlorine atom, an acetate group ($CH_3CO_2$) or a triflate group ($CF_3SO_3$); and * represents an asymmetric carbon atom whose configuration is inverted in the reaction.

3. The process according to claim 2, wherein a fluorosulfuric acid ester of optically active α-hydroxyester of the general formula [9], a Grignard reagent of the general formula [11] and a zinc catalyst of the general formula [10] are used as the fluorosulfuric acid ester, the Grignard reagent and the zinc catalyst, respectively; and wherein an optically active α-substituted ester of the general formula [12] is produced as the α-substituted ester

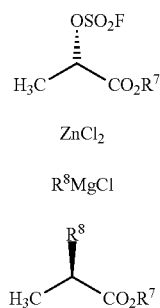
[9]

[10]

[11]

[12]

where $R^7$ represents a $C_1$-$C_6$ lower alkyl group; and $R^8$ represents an alkyl group.

4. The process according to claim 1, further comprising: forming the fluorosulfuric acid ester of α-hydroxyester by reaction of an alcohol of the formula [1a] with sulfuryl fluoride ($SO_2F_2$) in the presence of a base and water

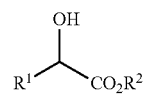
[1a]

wherein $R^1$ and $R^2$ have the same definitions as in the formula [1].

5. The process according to claim 2, further comprising: forming the fluorosulfuric acid ester of optically active α-hydroxyester by reaction of an alcohol of the formula [5a] with sulfuryl fluoride ($SO_2F_2$) in the presence of a base and water

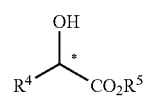
[5a]

wherein $R^4$, $R^5$ and * have the same definitions as in the formula [5].

6. The process according to claim 3, further comprising: forming the fluorosulfuric acid ester of optically active α-hydroxyester by reaction of an alcohol of the formula [9a] with sulfuryl fluoride ($SO_2F_2$) in the presence of a base and water

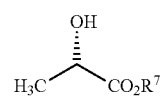
[9a]

wherein $R^7$ has the same definition as in the formula [9].

* * * * *